United States Patent [19]

Crosby, Jr.

[11] 4,426,875

[45] Jan. 24, 1984

[54] STRAIN MEASUREMENT

[75] Inventor: Edward L. Crosby, Jr., West Melbourne, Fla.

[73] Assignee: RCA Corporation, New York, N.Y.

[21] Appl. No.: 330,377

[22] Filed: Dec. 14, 1981

[51] Int. Cl.[3] .............................................. G01N 3/30
[52] U.S. Cl. ......................................... 73/12; 73/834
[58] Field of Search .................... 340/665, 668; 73/12, 73/791, 781, 830, 834

[56] References Cited

U.S. PATENT DOCUMENTS

| | | | |
|---|---|---|---|
| 1,921,624 | 8/1933 | Lewis | 73/12 X |
| 2,323,724 | 7/1943 | Nadai et al. | 265/13 |
| 2,362,589 | 11/1944 | Simmons, Jr. | 73/89 |
| 2,475,614 | 7/1949 | Hoppmann et al. | 73/12 |
| 2,660,880 | 12/1953 | Vivian | 73/12 |
| 3,196,671 | 7/1965 | Dannis | 73/781 X |
| 3,287,964 | 11/1966 | Dennis et al. | 73/830 X |
| 3,538,743 | 11/1970 | Glidden | 73/12 |
| 3,777,557 | 12/1973 | Dunlap et al. | 73/830 X |
| 3,798,631 | 3/1974 | Langford | 340/668 X |
| 4,178,712 | 12/1979 | Williams | 340/668 X |
| 4,266,217 | 5/1981 | Kao et al. | 340/668 X |

OTHER PUBLICATIONS

"Impact Resistance or Energy Absorbing Properties of Ropes of Nylon and 'Dacron'," DuPont Technical Information, Multi-Fiber Bulletin X-99, Feb. 1959.

Primary Examiner—Gerald Goldberg
Assistant Examiner—John E. Chapman, Jr.
Attorney, Agent, or Firm—Joseph S. Tripoli; Robert L. Troike; William Squire

[57] ABSTRACT

The elongation of a rope or cable under impact stress is measured by attaching a light emitting diode (LED) to a free-falling weight which loads the rope upon impact. The LED is turned on in response to a drive signal indicative of stress of the rope of greater than a given value. The lit LED and an adjacent scale are photographed to provide a record of the distance through which the LED moves, when on, and this indicates the amount of elongation of the rope to failure.

17 Claims, 11 Drawing Figures

STRAIN MEASUREMENT

The present invention relates to testing and more particularly to the measurement of strain induced in an article in response to applied stress.

In testing an article for strain, that is, in measuring its mechanical deformation, stress is induced by loading, i.e., by applying a measured force at a given rate (velocity) to the article. A strain test determines the energy absorbing characteristic of the material of which the article is made. During such a test in tension, the material usually elongates or stretches until it fails. The strain, at failure, of the material is known as the breaking strain. It is possible to easily measure the breaking strain of an article by loading it, in tension, at a relatively low rate. But such testing does not fully characterize some materials, such as synthetic textile fabrics, whose breaking strain and elongation characteristics are functions of the rate of loading.

Textile fibers, such as polyamid (Nylon), polyester (Dacron), aromatic amide (Kevlar), and others are currently finding use in cordage or ropes previously made of steel or manila. These textile fibers may have higher strength/weight ratios then steel or manila, are relatively impervious to corrosion and rot and have other desirable characteristics. However, the testing of such materials isn't as simple as for some other materials. As mentioned above, the strain introduced under slow loading differs from that introduced by high velocity loading, i.e., impact loading. The worst case loading, i.e., the most severe loading, occurs under impact conditions, and, therefore, it is desirable to measure the impact breaking strain of cords made of these materials. While the measuring of breaking strain under low rates of loading is relatively easy due to the low rate at which the cord elongates, impact strain measurement is extremely difficult due to the relatively high velocity at which the material elongates. That is, the movement is so rapid that it is difficult to record.

In U.S. Pat. No. 2,323,724 a high velocity tensile machine is disclosed which employs a light system to measure strain of a specimen. An anvil responsive to the stretching of a specimen under test partially blocks a beam of light to thereby reduce the amount of such light received by a photovoltaic cell. The reduced light response of the cell is recorded as a horizontal deflection of an electron beam moving across the screen of an oscillograph. However, the patent states this system requires frequent calibration, which may be attributed to drift in the system and which can cause measurement errors.

Another impact testing system, especially for ropes made of Nylon and Dacron, is disclosed in a brochure Multi-Fiber Bulletin X-99, February 1959, published by DuPont. In this testing system, ropes are tested for elongation and tension under impact or shock loading. A test tower includes a load cell, a device which produces an output voltage having a magnitude which is proportional to an applied tensile force, from which a rope under test is hung. A weight is attached to the lower end of the rope. A cone is also secured to the lower end of the rope. A dead weight is allowed to fall onto the cone. A potentiometer drive wire is attached to the weight. The potentiometer is "zeroed" before the drop. The rope stretches upon impact of the weight on the cone until the rope breaks. The distance of the drop of the weight including extension of the test specimen is traced by an oscillograph. The load is registered simultaneously.

There are a number of deficiencies inherent in this system. First, the load weight may be affected by the mechanical connection to the potentiometer. Because the weight is driving the potentiometer, the fall of the weight is not completely a free fall. The torque and friction loads induced by the connection of the weight to the potentiometer can introduce errors in the measurement of strain. Also, the potentiometer may introduce errors due to backlash or slippage in transmitting the displacement of the rope under test to mechanical rotation of the potentiometer shaft. Further, the potentiometer drive wire may stretch during operation and the potentiometer, under dynamic operation, may have inertia which can introduce error in the test.

In accordance with the present invention, the strain of an article under stress is measured by fixing to a point of reference one part of the article, and applying to a second part of the article a force sufficient to cause strain of the article between the first and a second part thereof. Means, including a point source of light, coupled to the second part of the article is responsive to stress of greater than a given value exhibited by the article, for providing a spot of light which remains on for the time the force is applied to the article and means are provided for recording the movement of the spot of light.

Figure 1:
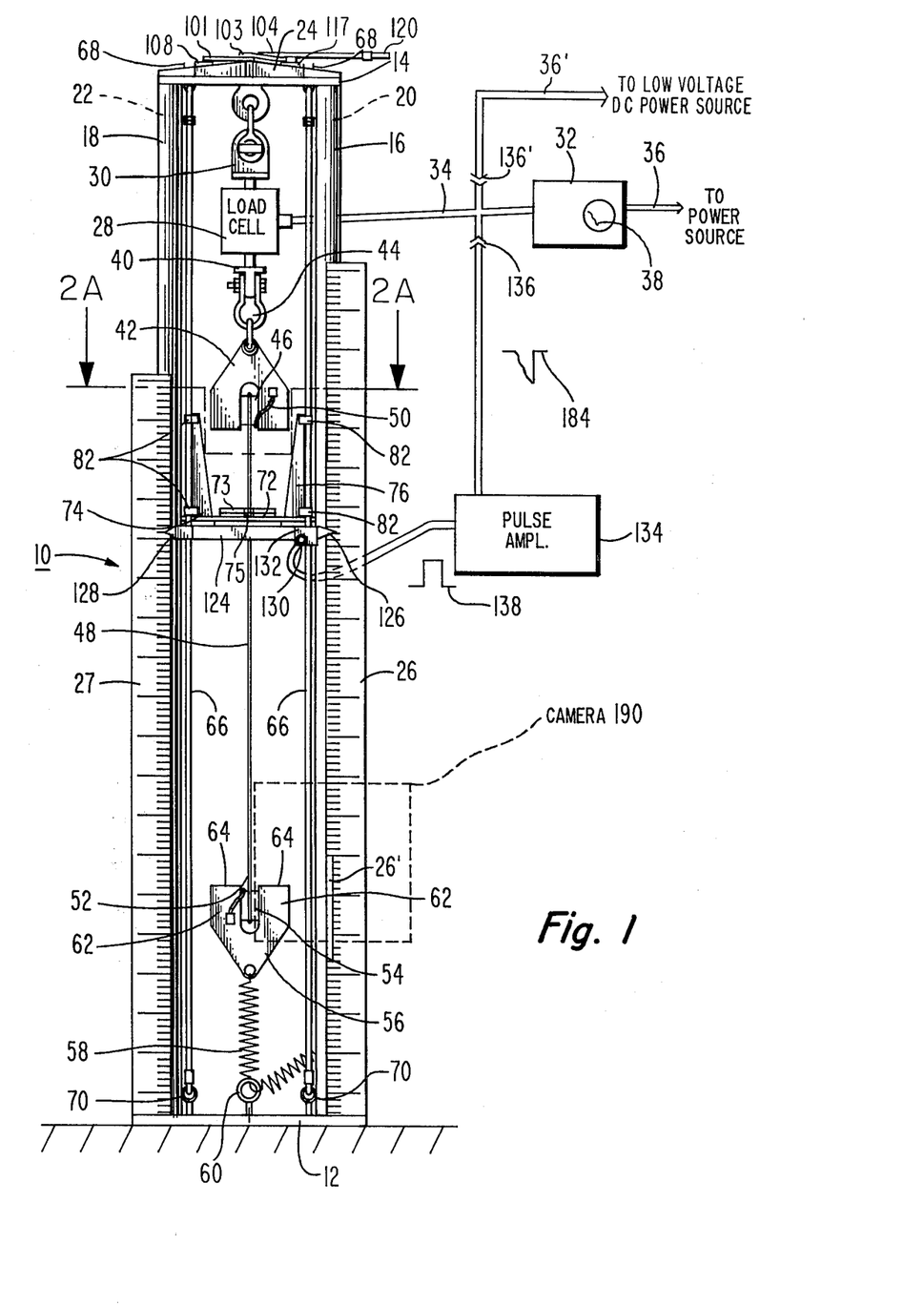
FIG. 1 is a front elevation view of an apparatus embodying the present invention.

In FIG. 1, test appartus 10 includes a tower structure which comprises a base plate 12, four pillars 16, 18, 20, and 22 and an upper plate 14. Pillars 16, 18, 20, and 22 may comprise hollow steel pipes welded at their ends to respective plates 12 and 14. The upper plate 14 is reinforced by cross ribs 24. A calibrated distance measuring scale 26 which may be calibrated in inches and decimals thereof is secured to pillar 16. A second scale 26', which may be a 12-inch machinist's scale, calibrated also in inches and decimals thereof is secured to and in front of scale 26. The scale 26' is calibrated to greater precision than scale 26 and may be, for example, calibrated in 0.01 increments as compared to 0.1 increments for scale 26. A third scale 27, also calibrated in inches and decimals is secured to pillar 18. Scales 26, 26', and 27 are for making measurements in the vertical downward direction. Load cell 28, more commonly known as a BLH load cell, is coupled to the upper plate 14 by shackles 30.

A load cell is a device which, when subjected to a tensile load force, produces an output voltage which represents the magnitude of the tensile force. The load cell output signal is coupled to the input of a storage oscilloscope 32 by two wires of the four wire cable 34. The load cell is powered by a low voltage D.C. source (not shown) connected to cable 36' which is connected to cable 34 by connector 136'. Oscilloscope 32 is powered from a conventional A.C. source at cable 36 and graphically displays on display 38 the waveform of the voltage produced by the load cell 28. The storage oscilloscope 32 is set to trigger automatically upon receipt of the input signal from the load cell 28. The sweep trigger threshold of the oscilloscope is set sufficiently high so that only a substantial output from the load cell 28 will cause it to sweep and display. The storage feature preserves the trace so that it may be observed at any convenient time after the event. The load cell 28 is accurately calibrated in millivolts "out" for pounds tension applied. By calibrating the amplitude function of the oscilloscope, that is, millivolts "in" versus centimeters deflection in amplitude, the peak tension force in pounds is obtained. This is the principal purpose of the scope. One can also read the time duration from the onset of tension until "break" by calibrating the sweep frequency of the oscilloscope.

The load cell 28 has a connecting link 40 to which a tensile force is applied to produce the output voltage signal on cable 34. The operation and construction of the load cell 28 is not described herein, as this device is commercially available.

A mandrel 42 is attached to link 40 by shackles 44. The mandrel 42 includes a circular cylindrical member 46 about which a rope 48, to be tested, is wrapped. End 50 of the rope is tied to the mandrel 42. As, during the test, this end of the rope is in relatively stationary position relative to the support, this end can be considered to be fixed to a point of reference. The circular shape of the cylinder 46 provides a smooth transition in connecting the rope to mandrel 42. This prevents sharp concentration of stresses in the rope at the mandrel. The rope extends vertically and its lower end 52 is wrapped around circular cylindrical member 54 of lower mandrel 56. During the test of the rope, the force is applied to the lower end of the rope and in response thereto the rope stretches and if the force is sufficiently great—equals or exceeds the impact breaking strain, the rope breaks. As will be explained, in one apparatus embodying the present invention, the elongation of the rope is observed and recorded by effectively observing the lower end of the rope.

Figure 2A:
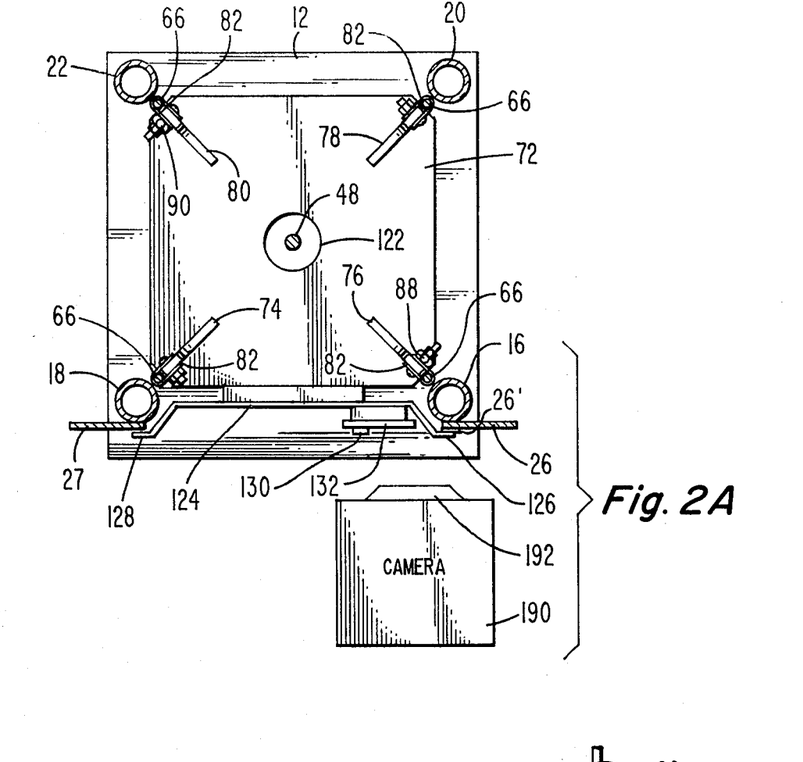
FIG. 2A is a sectional view of the apparatus of FIG. 1 taken along lines 2A—2A.
Figure 3:
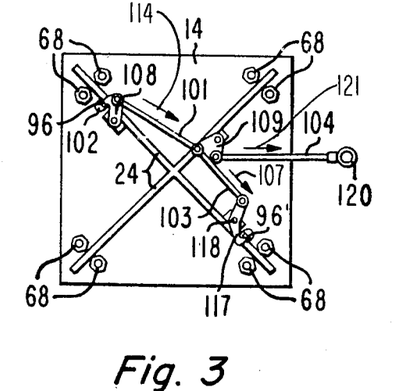
FIG. 3 is a plan view of the apparatus of FIG. 1.

The mandrel 56 is resiliently tied in position by spring 58 which passes through eyelet bolt 60 and which is secured to pillar 16. Mandrel 56 and spring 58 preload the rope with a force of about one pound. This force does not affect the output signal produced by cell 28 caused by an impact load. The mandrel 56 has a pair of upwardly extending legs 62 which terminate at surfaces 64 which are coplanar. Surfaces 64 lie in a plane which is perpendicular to the length dimension of rope 48. In FIGS. 1, 2A, and 3, four vertical guide cables 66, which may be steel ropes, are secured to the upper plate 14 by corresponding U-bolts 68 and to the base plate 12 by corresponding eye-bolts 70.

Suspended from upper plate 14, FIG. 1, is a carriage 72 which comprises a horizontal planar steel plate which may be generally square. Four upstanding ribs 74, 76, 78, and 80, FIG. 2A, which may be formed of steel are secured to plate 72. Ribs 76 and 80 are diametrically opposite and ribs 74 and 78 are diametrically opposite. Each of the ribs may be in a corner of the square formed by carriage 72 welded to the carriage 72.

Figure 2B:
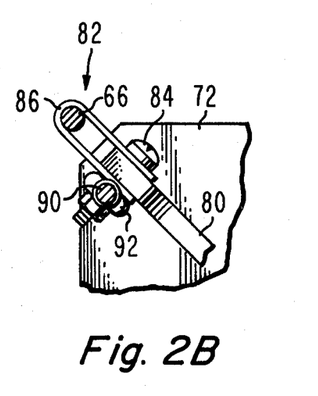
FIG. 2B is a plan sectional view of a portion of the apparatus of FIG. 1.
Figure 2C:
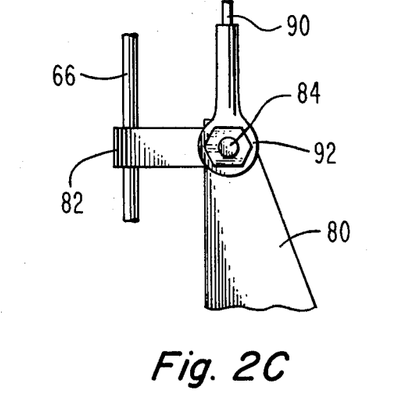
FIG. 2C is a side elevation view of the portion of FIG. 2B.

Each rib 74, 76, 78, and 80 has attached thereto at an upper end and a lower end, a cable guide clip 82, FIGS. 1, 2B, and 2C.

As shown in FIGS. 2B and 2C, guide clips 82 are U-shaped sheet metal members which are bolted by bolt 84 to a rib such as rib 80. The clips 82 on a given rib are one above the other so that a cable 66 passes vertically therethrough as shown in FIG. 1. The U end 86 of the clip, FIG. 2B, closely receives the cable 66 for guiding the carriage 72 as it moves in the vertical direction, FIG. 1, from the top to the bottom of the drawing.

Secured to diametrically opposite ribs, such as ribs 76 and 80, FIG. 2A, are carriage support cables 88 and 90, respectively. In FIG. 2C, cable 90, fitting 92 is secured to upper end of rib 80 by bolt 84. The fitting 92 is swaged to cable 90 similarly to the fitting 96 connection to the cable 90 shown in FIG. 5. Cable 88 is similarly secured to rib 76.

Figures 5, 6:
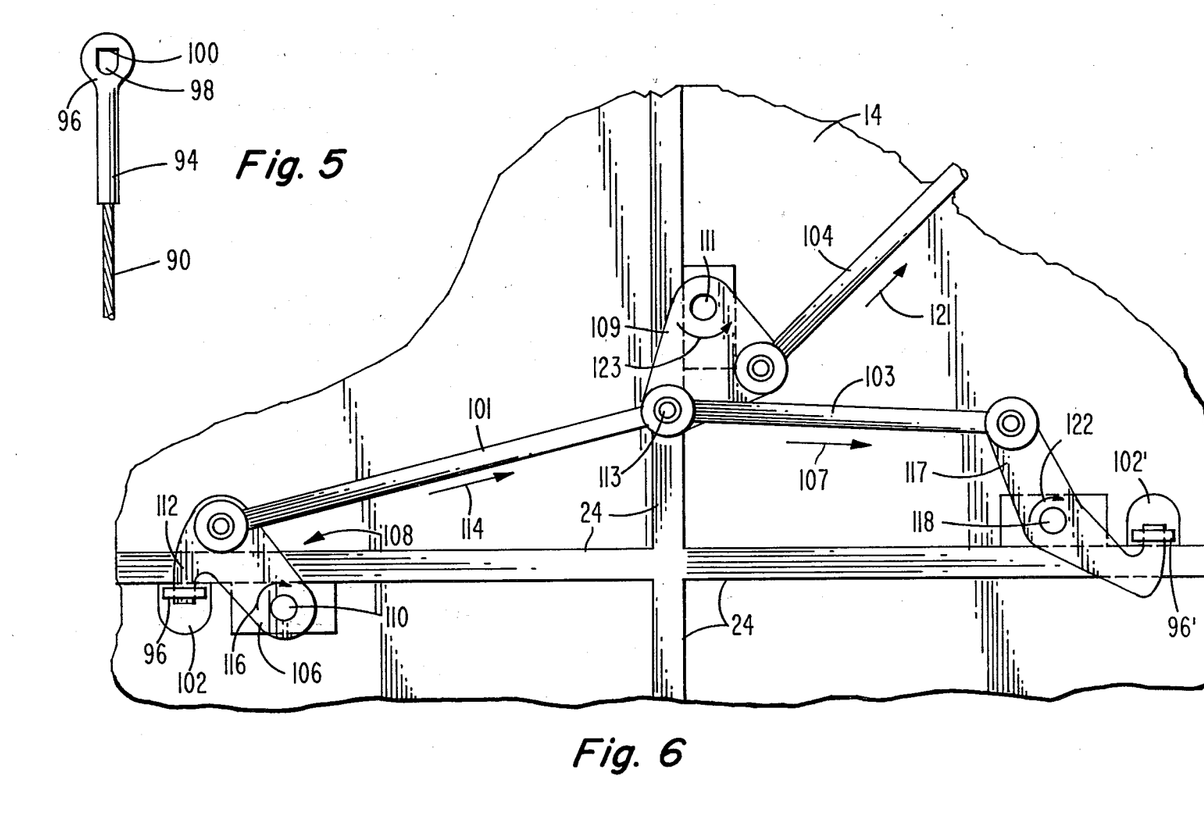
FIG. 5 is an elevation view of a portion of the apparatus weight release mechanism.
FIG. 6 is a more detailed view of the weight release mechanism.

In FIG. 5, the upper end of cable 90 is swaged at 94 to a fitting 96. Fitting 96 has a transverse aperture 98. The upper surface 100 of aperture 98 is flat. The upper end of cable 88 is similarly secured to a like fitting 96', FIGS. 3 and 6. The fitting 92, FIG. 2C, however, has a circular aperture rather than flattened as at 100, FIG. 5.

In FIG. 6, the upper plate 14, apertures 102, 102' are sufficiently large to permit the fittings 96, 96' to pass therethrough. One end of link 101 is pivotally secured to the junction of legs 106 and 112 of crank 108 and at its other end to a second crank 109 by pin 113. The leg 106 is pivotally pinned to plate 14 by pin 110. Leg 112 of crank 108 slips within the aperture 98 (FIG. 5) of fitting 96 abutting against the upper flattened surface 100, the leg 112 also being flattened on its mating surface. Crank 108 functions similarly to a sear (a pivoted piece in the firing mechanism of a pistol). When the link 101 is moved in direction 114, crank 108 rotates about pin 110 in direction 116 disengaging leg 112 from the fitting 96 by removing the leg from aperture 98. This action releases the fitting 96 and permits the fitting to drop through the aperture 102 in plate 14.

A third crank 117 is pivotally secured by pin 118 to plate 14. Crank 117 is pivotally secured to one end of link 103. The opposite end of link 103 is pivotally secured to pin 113 on crank 109. Crank 109 pivots about pin 111 which is rotatably secured to plate 14. The crank 117 is positioned and shaped so that movement of the link 103 in direction 107 as by rotation of crank 109 in direction 123 rotates crank 117 in direction 122 and disengages the crank 117 from fitting 96'. Actuating arm 104 is pivotally secured to crank 109. Movement of arm 104 in direction 121 pivots crank 109 in direction 123 moving links 101, 103 in respective directions 114 and 107, simultaneously disengaging the cranks 108 and 117, respectively, from the fittings 96 and 96'. This action releases carriage 72, permitting it to fall toward base plate 12, FIG. 1.

In FIG. 2A, rope 48 passes through central opening 122 in carriage 72 as the carriage 72 descends toward the base plate 12, FIG. 1. In FIGS. 1 and 2A, the carriage 72 has secured on the front side, the side facing the viewer in FIG. 1, a horizontally extending arm 124, which may be sheet metal and having pointers 126 and 128 at respective opposite ends of the arm. The pointers overlap distance measuring scales 26, 26', and 27 and indicate the position of the carriage 72 in the vertical direction.

Secured to the front of the arm is a light emitting diode (LED) 130 which is in about the same plane as the face of scales 26, 26' facing the bottom of the drawing, FIG. 2A. Diode 130 operates as an illuminated point when turned on. The diode should be a sufficiently high speed type so that it turns on and off in the low nanosecond range. Such a diode may be, for example, a gallium arsenide phosphide light emitting element having a 0.01 inch×0.01 inch emitting surface and may be a Radio Shack type TCR-121, Catalog No. 276-032. The diode as commercially available is encapsulated in an uncolored, clear compound and has a frosted hemispheric lens on the emitting face. For purpose of the present embodiment, the diode should emit a bright point light rather than an attenuated diffused light. The commercially available product is modified to provide such a light source by removing the hemisphere face such as by grinding and polishing. The diode 130 may be mounted on a small printed circuit board 132, FIG. 1. The printed circuit board 132 and surrounding structure around the diode 130, FIG. 1, are painted black to increase contrast between the point of light produced by the diode, when illuminated, and the surrounding surfaces.

In FIG. 1, the diode 130 is connected to a pulse amplifier 134 which, in turn, is connected by a coaxial connector jack 136 to the output cable 34 of the load cell 28. The amplifier may be powered by a battery (not shown) such as a 9-volt battery. The pulse amplifier 134 translates the negative-going voltage pulse produced by the load cell 28 into a positive-going square wave pulse 138 for driving the LED 130. The square pulse 138 is equal in duration to the pulse produced by the load cell 28 in response to the tensile force produced on the link 40 when the rope 48 is impact stressed. The LED 130 is lit for the time duration of the output pulse of amplifier 134.

In FIG. 2A, camera 190 is set on a tripod (not shown), with its optics 192 facing the expected position of the LED 130 at time of elongation of rope 48. The optics are focussed to present a sharp image of the LED 130, and scale 26'.

In operation, the carriage 72 initially is placed in the position shown in FIG. 1. Weights 73 comprising circular discs with slots 75 are placed on the carriage 72 with the rope 48 within the slots and the weights centered about the rope 48. The number and sizes of the weights are chosen to make total weight of the carriage 72 and the weights 73 a desired value.

The left and right scales 27 and 26, respectively, in FIG. 1 are used for static measurements, that is, for measurements made after the rope is in place but before the platform 72 and weights 73 drop. In particular, the left scale 27 is used to measure the effective drop distance (carriage 72 travel from the up or cocked position down to the point where the carriage 72 lower planar undersurface first impacts the lower mandrel). The right scale 26 is used to measure the specimen length, i.e., from its tangent point on the upper mandrel to the tangent point on the lower mandrel. These scales are read at the pointer positions. The scales may be located by moving them to the positions where the pointers read zero to 10 or other convenient number in the up position of the carriage and with a mounted, tensioned specimen cord in place. The up-down adjustment of the scales is provided by mounting clamps (not shown) which releasably secure the scales to the structural pipe frame pillars 16 and 18. The clamps may be worm-gear hose type clamps. Both scale positions are read before each "shot" or test and the drop distance and specimen length recorded. The drop distance and the weight in the test are used to calculate the energy delivered, and the impact velocity, if desired. The specimen length is the static length of which the instrumented elongated (LED photo-trace to be described later) is the percentage.

The third scale 26' which is used to make dynamic measurements is finished in satin chrome and bears finely engraved graduations. It is taped to the right-hand large scale in a vertical position which includes the distance over which the LED trace is expected to occur, which is, of course, from the LED position when the carriage 72 undersurface first impacts the lower mandrel surfaces 64, to the LED position at the point where the rope 48 breaks (when the LED turns off).

Figure 7:
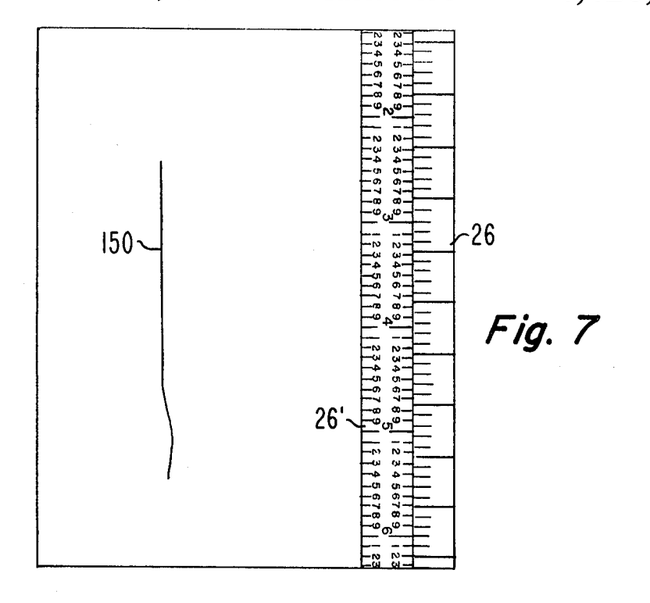
FIGS. 7, 8, and 9 are diagrams of different signal traces useful in explaining the present invention.

The use of the "fine" scale is essential to obtain accurate measurements and determines the apparatus' accuracy. (The scale 26' lies in substantially the same object plane as the LED.) The ultimate accuracy limitation is the size of the die of the LED which becomes luminous. It is the radius of the spot (taken as a circle) at each end of the trace which is the indeterminate part of the trace length, or in other words, the spot diameter, since $r \times 2 = d$. The pointer does not show in the resulting picture, as shown by FIG. 7, because it is black and moves very rapidly across the picture field. The scale 26' being 12 inches long, is at least as long as or longer than the greatest rope 48 elongation expected. The position of scale 26' is dependent on the length of the rope. Its position should be such that when the light emitting diode goes on, the diode is located close to the beginning (the upper portion) of the scale and the length of the scale 26' should be such that the light emitting diode has not passed beyond its lower end when the diode turns off. The position of scale 26' preferably is made adjustable to permit strain measurements to be made of rope specimens of different length.

Figure 4:
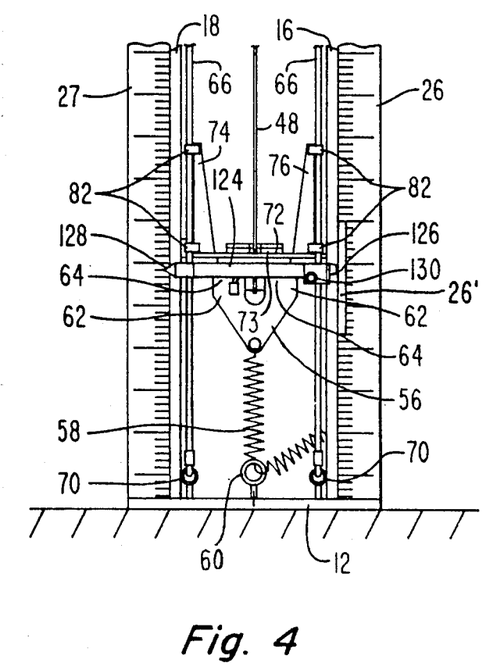
FIG. 4 is a partial front elevation view of the embodiment of FIG. 1 while a weight is being dropped.

In operation of the system, first, while the scale 26' is illuminated, the shutter of the camera 190 is opened for a time sufficient to expose a frame of the film to thereby record on the film a latent image of scale 26'. Then the lights are extinguished so as to place the apparatus and camera in darkness and the shutter of the camera is opened again and this time held open. It can be held open for some fixed interval sufficient to complete the measurement to be described and automatically closed at the end of the interval or it can be held open until manually closed when the measurement is completed. The carriage release arm 104, via handle 120, FIG. 3, is moved in direction 121, releasing the fittings 96 and 96'. This permits the carriage 72, FIG. 1, to free fall to the position shown in FIG. 4. The carriage 72 planar undersurface then impacts the upper coplanar surfaces 64 of the legs 62 of the mandrel 56. At this time the cell 28 begins to be loaded and starts to produce a measurable output voltage, which drives the LED on.

The camera 190 is positioned to record the output of the LED from the time it goes on, at impact of the platform with the mandrel 62, until the LED goes off when the rope breaks, a total travel distance which may be several inches. The LED 130 is in full view of and in focus of the camera during these several inches of travel. Impact of the carriage 72 on the mandrel 56 strains the rope 48 causing the load cell 28, FIG. 1, to produce the output negative pulse 184 on cable 34 as discussed. This pulse is amplified and squared by amplifier 134, FIG. 1. The squared pulse is applied to the LED 130, causing it to illuminate, creating a bright point of light for a time interval which accurately corresponds to the interval during which the rope is being strained. This light and its path of travel during strain of the rope is recorded by the film in the camera 190.

The LED 130 moves vertically in the downward direction in response to the movement of the carriage 72 and its accompanying weights. When the carriage 72 strikes the mandrel 56 and causes the rope being tested to exert on the load cell 28, a tensile load above a given magnitude, the cell 28 produces an output pulse 184 and that pulse remains on so long as the load exceeds this magnitude. The pulse amplifier 134 maintains the LED 130 illuminated in response to pulse 184. Tensile failure of the rope removes the stress from the rope and this removes the load from the load cell 28. The load cell thereby is disabled and its output pulse 184 is terminated, whereby pulse 138 is terminated and the LED 130 is extinguished. As previously mentioned, the shutter of the camera is opened when the apparatus is placed in the dark and this occurs before the start of pulse 138. After the pulse 138 terminates and while the apparatus is still in the dark, the shutter is closed either automatically or manually. During the time the LED is on, its movement is recorded on the same frame as was previously recorded the scale 26' and appears as a trace adjacent to (or over) the scale.

A schamatic showing of the above appears in FIG. 7 which illustrates the developed film. The streak 150 produced by the LED is adjacent to the scale and can be measured precisely by comparing its length with the image on the film of the scale 26'. By photographing the scale 26' and the light streak 150 on the same film frame and at the same focal distance, the magnification or minification distortions which could occur in recording the streak due to the particular optics of the camera used or variations in focal distances which might occur for different photographs are alleviated. The scale 26' is placed in the same object plane as the LED to insure equal magnification and image sharpness.

In the embodiment illustrated where the streak is adjacent to the scale, the elongation of the rope can be measured accurately by spanning the length of the streak 150 with dividers and using the dividers then to read the scale 26' image, FIG. 7. This gives an accurate measurement of the elongation of the tested rope 48. In a photograph corresponding to FIG. 7, the elongation of a particular 40.8 inch long polyester rope was measured as 3.04 inches—a 7.45 percent strain.

Figure 8:
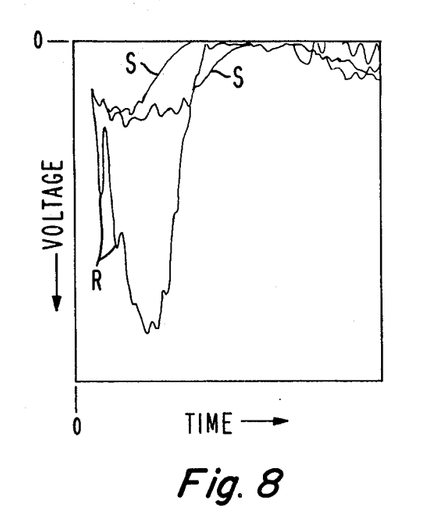
Figure 9:
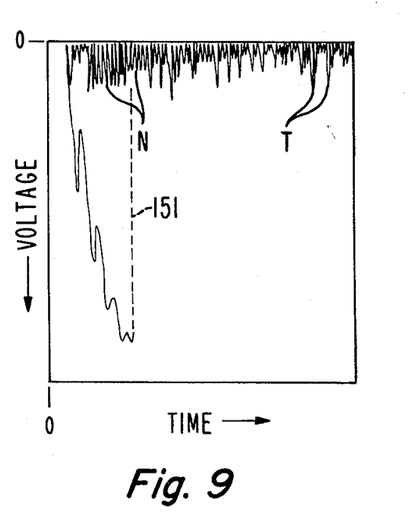

FIGS. 8 and 9 are graphs representative of photographs of oscilloscope display 38 and show various pulses produced by the load cell 28 under different conditions. In FIG. 8, the waveform shows a resultant tensile characteristic when the rope fails to break. The ragged form of the waveform at R shows resonance strumming or "twang" of the rope. The rope did not break due to insufficient energy input. The secondary sweeps at S were triggered by rebounds of the carriage 72. FIG. 9 shows tension on a cord under test in which the cord broke. The additional spikes T are due to rebounding hardware such as the shackles, mandrel and load cell at the rope upper end. Noise at N is due to ringing of the load cell shocked by the broken specimen rope. The peak force applied to the rope can be calculated for this particular load cell in a known manner. The fall of the load cell voltage shown by dashed line 151 occurs too quickly to be recorded on the display 38 trace.

Thus, as described, an impact force is applied to an article (the rope) at one point (where it meets lower mandrel 56) while a second point on the article (where it meets upper mandrel 46) is fixed to a point of reference. A radiation emitting element (LED 130), is moved through a distance which is equal to the amount of elongation imparted to the article (rope) before it breaks. While in the present example, the radiation detected comprises directly emitted light, once could detect reflected light instead. For example, the light could be sensed after reflection from pointer 126 made of light reflective material, with the light source fixed to a point of reference and turned on in response to the pulse amplifier 134.

While in the example shown, the LED, when on moves through a distance equal to the amount of rope elongation required to break the length of rope being tested, by using a reflector, one can obtain an amount of light reflection which can be recorded. Such a system can employ a light source such as a narrow fan beam of light incident on and extending along the expected path of the pointer 126 at the location of camera 190. The fan beam radiation would reflect from a point reflector on the pointer such as a small mirror (not shown) and then be recorded by camera 190. The fan beam light source would be turned on by amplifier 134.

While the present embodiment illustrates a tensile load, it should be equally apparent that a compressive load created by an impacting force may also be employed with an LED for measuring the compressive strain of such an article. Also while the present strain as shown here is induced by a free-falling weight, it should be understood that machine-induced stresses, as known in the art, may also be employed to strain an article under test. An important feature of the present system, whatever strain it is measuring, is that the means which records the radiation produced by the LED or other radiation device also record the scaling means such as scale 26' to reduce errors in the measurement of strain.

What is claimed is:

1. A method for measuring the strain induced on an article in response to an impact stress applied to the article comprising:
    fixing to a point of reference one part of the article;
    applying an impact force to another part of said article to stress and thereby strain the article between the parts;
    placing in fixed spaced relation to one of said parts of the article at least during the application of said impact force an element which in one condition operates as a point source of radiation and which in a second condition is non-radiating;
    placing said element in its one condition when the stress exhibited by the article exceeds a given value and in its second condition when said stress is lower than said given value; and
    recording on a radiation responsive medium placed in fixed spaced relation to the other of said parts, the relative movement of said element to said medium resulting from the strain of the article caused by said stress while the element is in its one condition.

2. A method of determining the elongation of an article when it is stressed comprising the steps of:
    fixing to a point of reference a first part of the article;
    applying an impact stress to a second part of said article in a sense to cause elongation of said article between the first and second parts thereof;

placing in fixed spaced relation, at least during the application of the impact stress, to one of the parts of the article an element capable of operating as a point source of light when in a first condition and which is off in a second condition;

placing said element in its first condition when the impact stress imparted to the article exceeds a given value and in its second condition when the stress in the article is lower than said given value; and recording an image of the relative movement of said element to the other part of the article caused by the stress induced elongation of the article when the element is in its first condition.

3. An apparatus for determining the strain imparted to an article in response to a stress applied between first and second parts of the article comprising:

means for fixing to a point of reference said first part of the article;

means for applying an impact force to said article at the second part thereof for stressing and thereby straining said article between said two parts thereof;

signal generator means including a radiating source in fixed spaced relation, at least during the application of the impact force, to one of said parts of said article for generating a radiating signal in response to stress applied to said article, the source moving relative to the other part of said article in response to the strain of said article caused by said force applied to said article, said signal generator means including a means responsive to the stress applied to said article for turning on said radiating source when said stress exceeds a given value and for turning off said radiating source when said stress is lower than said given value; and means responsive to the radiation of said signal for sensing said relative movement of said source to said other part of said article in response to the force applied to said article.

4. The apparatus of claim 3 wherein said signal generator means source comprises a point source of light.

5. The apparatus of claim 4 wherein said source of light is fixed in said spaced relation to said second part and further including a scale fixed to said point of reference and located adjacent to said point source of light and, wherein said means for sensing movement comprises a light recording medium fixed in said spaced relation to said first part for recording both said scale and the image of said light source adjacent thereto.

6. An apparatus for measuring the elongation of a cable under dynamic impact breaking stress comprising:

a support structure;

first means adapted to secure said cable to said structure at one portion of said cable;

means coupled to said cable and responsive to stress applied to said cable for generating an output signal representative of the magnitude of said stress;

second means adapted to be secured to said cable at a second portion of said cable vertically beneath the first means;

third means including a weight of a desired value, said weight adapted to drop through a desired distance onto said second means, for inducing a force on said second means sufficient to cause said cable to elongate and then to break;

radiation emitting means secured to said third means responsive to said output signal when it represents a value of stress greater than a given value for turning on said radiation emitting means and turning off said emitting means when said output signal represents a value of stress lower than said given value;

distance scaling means adjacent said emitting means when the latter is turned on for providing a distance scale along which said light emitting means moves when it is turned on; and recording means adjacent said scaling means for recording an image of said scaling means and an image of said radiation emitting means during the movement of said radiation emitting means while it is on.

7. The apparatus of claim 6 wherein the distance scaling means is located in substantially the same object plane as said radiation emitting means, and wherein said recording means records the image of said radiation emitting means at a different time than it does of said scaling means.

8. The apparatus of claim 6 or claim 7, wherein said radiation emitting means comprises a point source of light.

9. An apparatus for measuring the change in shape of an article in the direction of an applied force while the article is being stressed comprising:

means for fixing to a point of reference a first part of the article;

means for applying to a second part of the article an impact force sufficient to cause impact strain of said article between said first and second parts thereof;

means including a point source of light coupled to said second part of said article responsive to stress of greater than a given value exhibited by said article, for providing a spot of light which remains on only for the time said stress exceeds said given value; and means for recording the movement of said spot of light.

10. The apparatus of claim 9 further including a scale adjacent to said spot of light oriented to measure the distance through which the spot moves, said means for recording being arranged to record both said scale and said spot of light.

11. The apparatus of claim 10 wherein said means for applying force includes means for applying said force in a direction to elongate said article.

12. A method for measuring the change in shape of an article in the direction of an applied force while the article is being stressed comprising:

fixing to a point of reference a first part of the article;

applying to a second part of the article a force sufficient to cause impact breaking strain of said article between the first and second parts thereof;

illuminating a point source of light coupled to said second part of said article in response to stress of greater than a given value exhibited by the article for providing a spot of light which remains on between the time the force is applied to the article and the time the article fails; and recording the movement of the spot of light.

13. The method of claim 12 wherein said force applying step includes applying said force in a direction to elongate the article.

14. Apparatus for determining the elongation imparted to an article in response to an impact stress applied between first and second parts of the article comprising:

means for fixing to a point of reference said first part of the article;

means for applying an impact force to the article at the second part thereof for impact stressing the article between the two parts;

means for emitting a point source radiation signal at said second part of the article in response to the force being applied to the article; and means for recording the movement of said signal during the time of occurrence of the stress.

15. A method of determining the strain of a rope in response to a stress applied between first and second ends of the rope comprising:

supporting the rope at its upper end, the rope extending vertically;

applying a downward force in response to a free-falling weight to the lower end of the rope to strain the rope;

emitting a radiation signal from a point source or radiation coupled to said lower end of said rope, only during the period the rope is stressed by said force;

recording on a storage medium the movement of said radiation signal; and measuring on the recording medium the length of the trace made by the recorded radiation signal.

16. In a test apparatus for determining the strain of a rope in response to an impact force on the rope including a tower structure, device means secured to the structure for producing a signal representative of the magnitude of stress in said rope, said rope being coupled to said device means and extending vertically downward therefrom, and a movable carriage and weight means thereon adapted to free fall and impact means secured to the lower end of the rope for inducing impact stress on the rope, the improvement comprising:

radiation emitting means secured to said carriage means and responsive to said device means for producing radiation in response to said signal, when said signal represents a stress of greater than a given magnitude; and means responsive to the radiation emitted by said emitting means for recording the distance through which said emitting means travels during the time it is producing radiation.

17. The apparatus of claim 16 wherein said device means includes means for producing a voltage pulse and means for amplifying and shaping said pulse, and wherein said radiation emitting means comprises a point source of light.

* * * * *